United States Patent [19]

Butsch

[11] Patent Number: 5,236,053

[45] Date of Patent: Aug. 17, 1993

[54] TORQUE SYSTEM

[75] Inventor: Otto R. Butsch, Running Springs, Calif.

[73] Assignee: Aseptico, Incorporated, Woodinville, Wash.

[21] Appl. No.: 883,556

[22] Filed: May 15, 1992

[51] Int. Cl.$^5$ .............................................. B25B 23/14
[52] U.S. Cl. .................................... 173/176; 173/217; 81/467
[58] Field of Search ..................... 173/217, 176, 178; 81/467, 479; 310/47, 46, 50, 96, 97, 103, 15, 20

[56] References Cited

U.S. PATENT DOCUMENTS

| | | | |
|---|---|---|---|
| 796,259 | 8/1905 | Sherman | 310/20 X |
| 2,537,997 | 1/1951 | Hattan | 81/479 |
| 2,682,796 | 7/1954 | Larson | 81/479 |
| 2,881,636 | 4/1959 | Palmleaf | 74/524 |
| 2,924,134 | 2/1960 | Harmes | 81/52.4 |
| 3,240,304 | 3/1960 | Wickersham | 310/103 X |
| 3,895,517 | 7/1975 | Otto | 73/88.5 R |
| 4,314,490 | 2/1982 | Stone | 81/479 |
| 4,359,906 | 11/1982 | Cordey | 73/862.23 |
| 4,486,176 | 12/1984 | Tardieu et al. | 310/103 X |
| 4,669,319 | 6/1987 | Heyraud | 73/962.23 |

Primary Examiner—Frank T. Yost
Assistant Examiner—Rinaldi Rada
Attorney, Agent, or Firm—James Richard Vance

[57] ABSTRACT

Magnetically controlled torque system or wrench for turning a fastener in a controlled manner until a variable and selectable maximum torque value is achieved whereupon the torque system is rendered inoperative, the maximum torque value being determined by the amount of force required to decouple a plunger from a magnetic field.

5 Claims, 8 Drawing Sheets

TORQUE SYSTEM

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyrights whatsoever.

TECHNICAL FIELD

This invention relates to apparatus and processes for turning a fastener, such as a nut, bolt, or dental prosthetic device, to insert the fastener into a desired medium or to remove the fastener from such medium. More particularly, the present invention relates to apparatus and processes employing a wrench having a variable and selectable maximum torque value that can be reached during use.

BACKGROUND ART

Torque devices are commonly used within the automotive and industrial industries. Such torque devices typically have internal mechanics and/or a flexible handle that cause a rigid pointer to move in response to an applied force of torque. A gauge is located adjacent to the pointer to indicate the amount of torque being exerted.

Devices using the same principles, but greatly reduced in size, are used by dentist and surgeons to install various prosthetic devices within humans.

Such devices, however, are not without difficulties. For example, when a dental implant is embedded within the jaw of a human, the amount of room available to manipulate the torque device is extremely limited.

Furthermore, the post, head, and/or abutment screw of the prosthesis are usually so small and delicate that both the medical practitioner and the patient face severe dangers if insufficient and/or excessive torque forces are used. If insufficient torque forces are used, the prosthesis may be improperly secured to the jaw of the patient and may become dislodged, bent, and/or broken. If excessive torque forces are used, the head, post, and/or abutment screw may be sheared off, with a portion of the prosthesis remaining within the patient's jaw. If any of these events occur, the patient is exposed to a health danger and the medical practitioner is exposed to an allegation of malpractice and liability.

The following disclosures relate to various known types of torque devices: Palmleaf (U.S. Pat. No. 2,881,636; issued Apr. 14, 1959); Harmes (U.S. Pat. No. 2,924,134; issued Feb. 9, 1960); Otto (U.S. Pat. No. 3,895,517; issued Jul. 22, 1975); Stone (U.S. Pat. No. 4,314,490; issued Feb. 9, 1982); Cordey (U.S. Pat. No. 4,359,906; issued Nov. 23, 1982); and Heyraud (U.S. Pat. No. 4,669,319; issued Jun. 2, 1987).

The inventor believes that the cited disclosures taken alone or in combination neither anticipate nor render obvious the present invention. These citations do not constitute an admission that such disclosures are relevant or material to the present claims. Rather, these citations relate only to the general field of the disclosure and are cited as constituting the closest art of which the inventor is aware.

DISCLOSURE OF INVENTION

The present invention is designed to overcome the previously stated difficulties and disadvantages. Furthermore, the invention provides an extremely accurate adjustable torque wrench that can be effectively used even in situations where access is dramatically limited. The invention provides apparatus and processes to rotate a fastener with a variable and selectable maximum torque force without over-torquing the fastener. The torque value is easily adjusted without requiring physical modification or specific observation of the handheld apparatus or implement. The apparatus can also be used to remove the fastener.

More particularly, the present invention is specifically designed for use within the medical and dental professions to secure medical implants within humans. For example, the apparatus and processes taught herein may be used to turn a fastener, such as a nut, bolt, or dental prosthetic device, and thereby insert the fastener into bone. The invention may also be used to remove the fastener from bone. Alternatively, this invention may be enlarged and strengthened for use within the automotive, aeronautical, and industrial industries.

The present invention accomplishes the foregoing objectives by using an elongated housing having a handle portion at one end and a working end at an opposite end. The handle portion of the housing is hollow and contains an electrically operative magnetic stator. An elongated plunger is located longitudinally within the housing extending from the handle portion to near the working end of the apparatus.

One end of the plunger has a flange thereon which can be magnetically urged to contact a corresponding flange on the stator. When an electrical current passes through a series of coils wrapped around the stator, a magnetic field is generated. The magnetic field urges the flange of the plunger to operatively engage the flange of the stator. Thus positioned, the plunger is magnetically coupled to the stator. In essence, the stator and plunger function very similar to that of a solenoid. When the forces exerted against the plunger in a direction away from the stator flange exceed the magnetic attraction, the plunger decouples from the stator.

A flexible spring is operatively secured to an opposite end of the plunger. The flexible spring is positioned longitudinally within the housing and is generally collinear with the plunger.

A ratchet mechanism is operatively secured to the apparatus within the working end of the housing. The ratchet mechanism is rotatable within the working end of the housing.

The ratchet mechanism has a centrally located keyed chamber or cylinder into which the fastener and/or an extension device may be secured. The keyed chamber or cylinder is positioned in collinear or concentric alignment with the fastener and/or extension device to define an axis of rotation. The keyed chamber or cylinder restricts rotational movement between the fastener and/or extension device and the ratchet mechanism. The ratchet mechanism also has outwardly extending, radially protruding ratchet teeth which encompass the circumference of the ratchet system.

When the plunger flange is magnetically coupled to the stator flange, the distal end of the flexible spring is urged into physical engagement with the outwardly extending teeth of the ratchet mechanism.

Pivotal rotation of the housing in a tightening direction about the aforesaid axis causes the flexible spring to engage the ratchet teeth at an eccentric angle thereto and urge the ratchet mechanism to rotate. In essence, the distal end of the flexible spring serves as a pawl to urge the teeth of the ratchet mechanism to rotate about the aforesaid axis.

When the housing reaches a barrier that defines the limits of its tightening stroke, the rotation of the housing is reversed. As the housing passes through its reverse stroke, the flexible spring deflects to pass over and not operatively engage successive teeth of the ratchet system.

Once the housing has reached the limits of its reverse stroke, the tension within the flexible spring urges the distal end or pawl of the flexible spring into the recess between successive adjacent teeth of the ratchet mechanism.

Renewed rotation of the housing in a tightening direction will urge the flexible spring into operative engagement with the teeth, causing the ratchet mechanism to again rotate.

During tightening rotation of the housing, an operative force is exerted by the distal end of the flexible spring against the teeth of the ratchet mechanism. A reactive force, which is opposite in direction to the operative force, is transmitted along the length of the flexible spring toward the plunger. The reactive force is transmitted from the flexible spring into and along the length of the plunger until an opposite force is exerted on the plunger by the electrically operative magnetic stator.

If the reactive force is less than or equal to the opposite force exerted on the plunger by the magnetic stator, tightening rotation of the ratchet system will be achieved.

If the reactive force is greater than the opposite force exerted on the plunger by the magnetic stator or solenoid, the plunger decouples from the magnetic stator. Decoupling of the plunger from the magnetic stator causes the plunger and flexible spring to move away from and disengage the ratchet mechanism. In other words, decoupling of the plunger from the magnetic stator renders the ratchet system inoperative.

By controlling the amount of opposite force exerted on the plunger by the magnetic stator or solenoid, the amount of torque that can be exerted on the ratchet system can be controlled. If the controlled torque is exceeded, the plunger simply decouples from the magnetic stator or solenoid and the ratchet system is rendered inoperative.

In an alternative embodiment, the plunger and magnetic stator or solenoid may be provided with means to magnetically power and urge longitudinal movement of the plunger back and forth within the interior of the housing. This allows the engagement and retraction of the flexible spring against successive teeth of the ratchet mechanism to be mechanically automated in a controlled indexed manner until a desired torque force is achieved. The flexible spring can move forward to engage a particular tooth and then flex outwardly to retract and engage the next successive tooth of the ratchet mechanism. Thus operated, the housing does not even have to be rotated to turn a fastener to a given torque. This feature is extremely advantageous when access for rotation of the housing is limited or restricted.

The plunger, as described above, may further be provided with a reverse pawl or prong located at a distal end of the plunger near the teeth of the ratchet mechanism. The reverse pawl is positioned to engage and urge rotation of the ratchet mechanism in a direction opposite to that caused by the flexible spring.

When removal of the attachment means or fastener, such as a screw, bolt, nut, prosthesis or the like, is desired, the flexible spring is simply urged away from engaging the teeth of the ratchet mechanism. Once the flexible spring is disengaged, the plunger is urged forward until the reverse pawl engages the teeth on the opposite side of the ratchet mechanism. The housing and handle may then be rotated and manipulated to manually rotate the ratchet mechanism in an opposite, removal direction, and thereby remove the attachment means from the medium or material.

These and other objects and advantages of the present invention will become more readily apparent upon reading the following disclosure and referring to the attached drawings.

One should understand that the drawings are not necessarily to scale and the elements are sometimes illustrated by graphic symbols, phantom lines, diagrammatic representations, and fragmentary views. In certain instances, the inventor may have omitted details which are not necessary for an understanding of the present invention or which render other details difficult to perceive.

BEST MODE FOR CARRYING OUT THE INVENTION

Figures 9, 10:
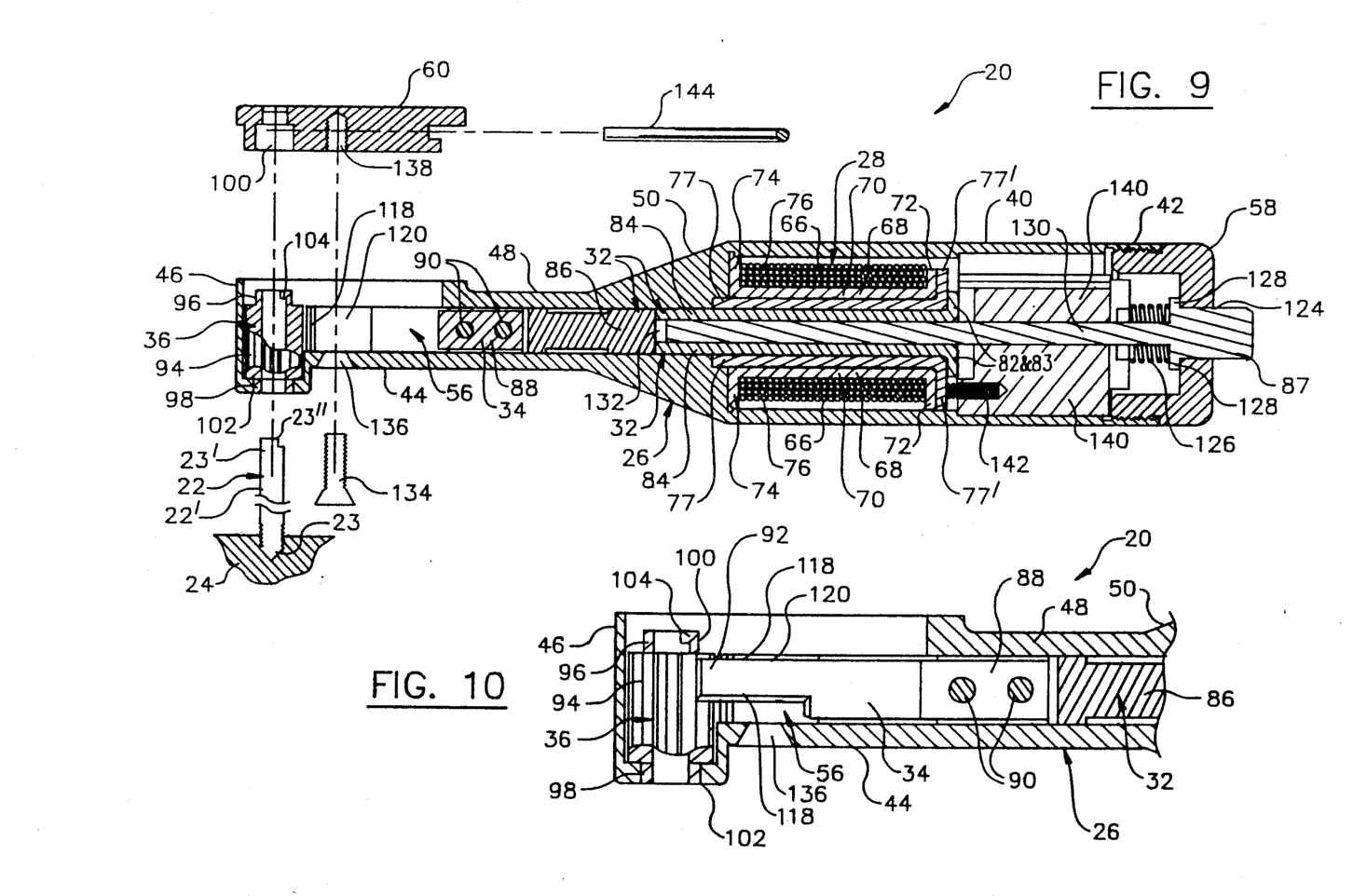
FIG. 9 is an exploded, cross-sectional view of the invention as seen in FIG. 4 with the various internal components and elements inserted therein.
FIG. 10 is a partial, cross-sectional, side-elevational view of the invention as seen in FIG. 9 further illustrating the engagement of the flexible spring with the teeth of the ratchet mechanism.

Referring to the drawings, wherein like numerals indicate like parts, as best seen in FIG. 9, torque system or apparatus 20 of the present invention is used to turn attachment means 22 within a material 24. As explained above, attachment means 22 may comprise a screw, bolt, nut, pin, prosthesis, or other similar article which is intended to be screwed into material 24. For example, attachment means 22 may comprise a post 22' having a first end 23 and a second opposed end 23'. First end 23 is capable of being turned to extend into material 24. Second end 23' has a head 23" thereon which can engage and be rotated by apparatus 20.

Material 24 may comprise any desired medium, such as bone, wood, metal, plastic, synthetic material, or the like.

To accomplish the foregoing task, apparatus 20 generally comprises the combination of an elongated housing 26, means 28 for producing a controlled magnetic field (not illustrated), an elongated plunger 32, an elongated flexible spring 34, a ratchet mechanism 36, and means 38 (not illustrated) for adjustably controlling the magnetic field and the magnetic forces related thereto.

Housing 26 may take any form which appropriately orients apparatus 20 with respect to material 24 into which attachment means 22 is to be secured and/or removed. As illustrated, housing 26 has a handle portion 40 located at one end 42. A ratchet portion 44 is located at an opposite end 46 of housing 26. An elongated shaft portion 48 is located between first end 42 and second end 46 of housing 26.

Handle portion 40 is dimensioned to accommodate the placement of various elements therein, as will be discussed further below. Handle portion 40 is also dimensioned to fit comfortably within the hand of a user (not illustrated).

Shaft portion 48 is dimensioned to allow for its entrance into and removal from a small access opening (not illustrated). Consequently, the diameter of shaft portion 48 is substantially reduced in comparison to the diameter of handle portion 40.

The access opening may comprise simply the mouth of a person, as would occur if this invention was used in the dental surgery profession. Alternatively, the access opening may comprise an incision, any access opening to machinery, etc.

Figures 1, 2:
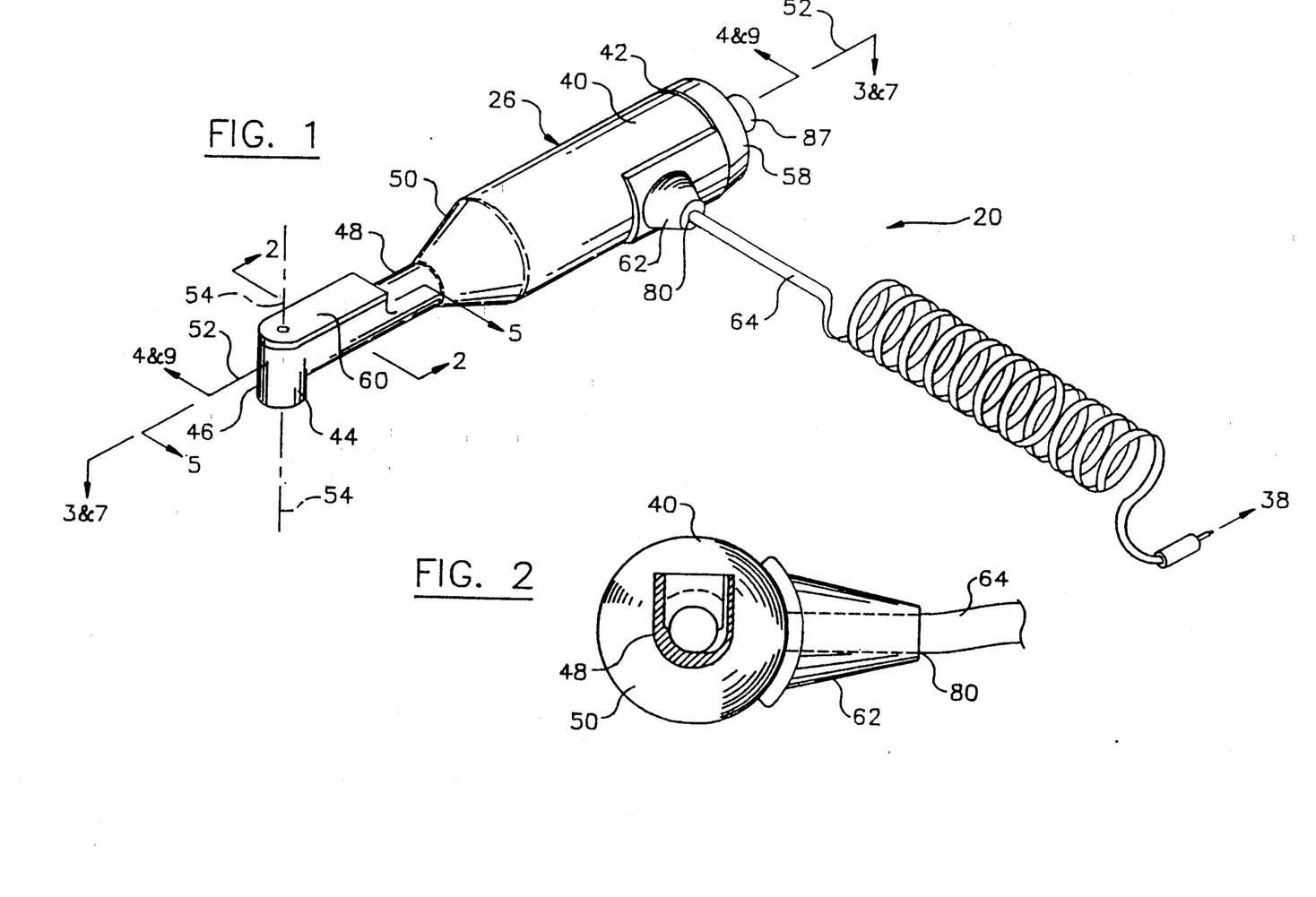
FIG. 1 is an isometric view of the first embodiment of the present invention illustrating the general configuration of the device and the planes through which various views are taken.
FIG. 2 is a cross-sectional view of the housing as seen along a plane defined by line 2—2 in FIGS. 1 and 3 with the lid removed.
Figure 3:
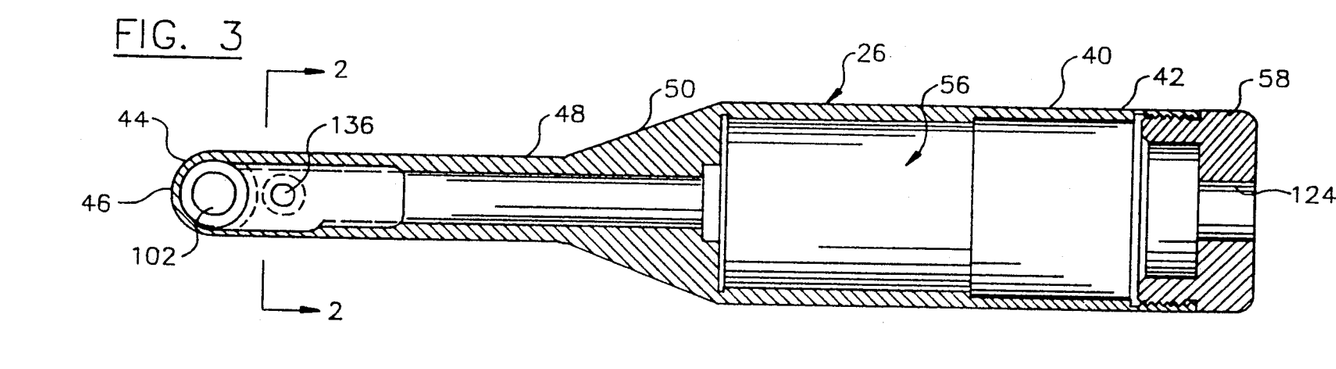
FIG. 3 is a cross-sectional view of the housing as seen along a plane defined by line 3—3 in FIG. 1.
Figure 4:
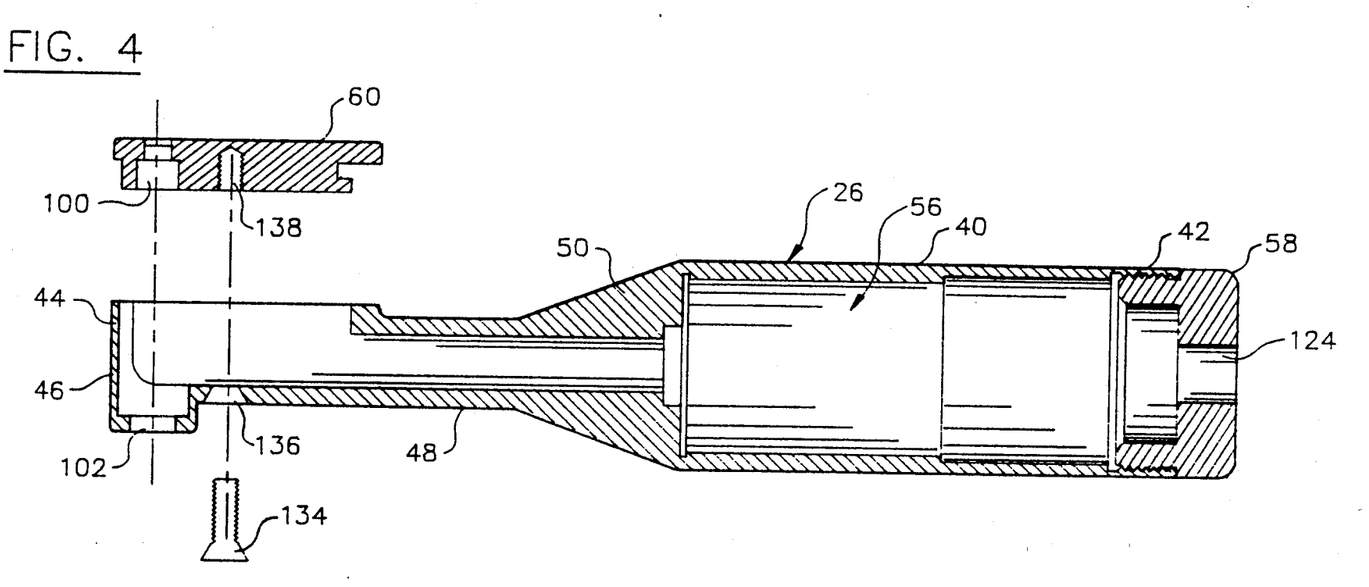
FIG. 4 is an exploded, cross-sectional view of the housing as seen along a plane defined by line 4—4 in FIG. 1.
Figure 5:
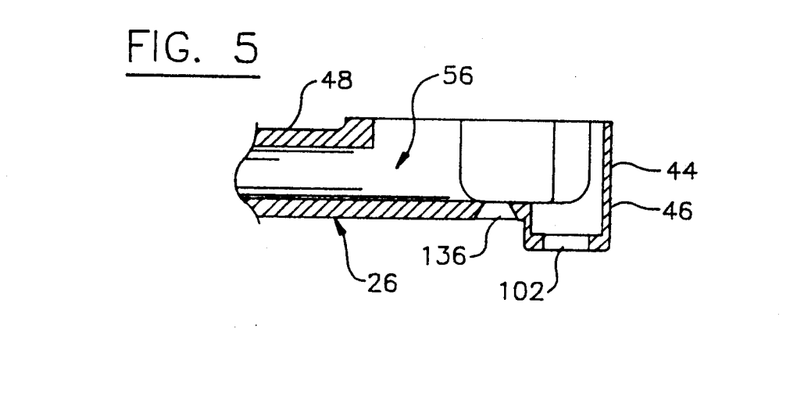
FIG. 5 is a partial, cross-sectional view of the ratchet portion of the housing as seen along a plane defined by line 5—5 in FIG. 1.

Shaft portion 48 extends longitudinally outwardly from handle portion 40. The transition from handle portion 40 to shaft portion 48 may be gradual as illustrated by the integral tapering collar portion 50. Handle portion 40 and shaft portion 48 are also oriented to each other in such a manner that they share a common longitudinal axis 52 (best seen in FIG. 1).

Ratchet portion 44 is dimensioned to accommodate the placement of various elements therein. However, the outer dimensions of ratchet portion 44 are reduced in size relative to handle portion 40. The size of ratchet portion 44, however, should be sufficient to accomplish the task of turning attachment means 22 into or out of material 24. Ratchet portion 44 defines a rotational axis 54 which intersects longitudinal axis 52.

Housing 26 defines an enclosure 56 within which magnetic means 28, plunger 32, flexible spring 34, and ratchet mechanism 36 are contained. Magnetic means 28 is generally contained within handle portion 40 of enclosure 56. Plunger 32 is generally contained within handle portion 40 and shaft portion 48 of enclosure 56. Flexible spring 34 is generally contained within shaft portion 48 of enclosure 56. Ratchet mechanism 36 is generally contained within ratchet portion 44 of enclosure 56.

Housing 26 may further comprise an end cap 58 that is secured to a distal end of handle portion 40. Housing 26 may further comprise a ratchet cover plate or lid 60 that seals and protects the inner workings of ratchet mechanism 36. Housing 26 may also comprise strain relief means 62 that prevents abrasion of an electrical cord 64 that enters housing 26.

Means 28 for producing a controlled magnetic field generally comprises an electrically powered stator 66 positioned within handle portion 40 of enclosure 56. For example, stator 66 may comprise a bobbin 68 having a central hollow cylinder 70 and a first flange 72 at one end thereof and a second flange 74 located an the other end thereof. An electrically conductive coil 76 is wrapped in successive helixes around bobbin 68 between first flange 72 and second flange 74 to create a solenoid. Coil 76 is then operatively connected to electrical cord 64.

Stator 66 may simply comprise an electrically operative bobbin 68 and coil 76. Alternatively and preferably, stator 66 also comprises a hollow tube 77 having an outwardly radiating flange 77'. Tube 77 is placed within central hollow cylinder 70 and flange 77' is juxtaposed into magnetic unison with first flange 72.

Electrical cord 64 is passed through a hole or opening 80 in housing 26 to a controlled source of electrical power (not shown). The passage of cord 64 through housing 26 may be protected by the use of strain relief means 62. In essence, strain relief means 62 acts as a shock absorbent barrier against which cord 64 is urged when apparatus 20 is used.

The passage of an electrical current through cord 64 and coil 76 causes a magnetic field to be produced around bobbin 68. The magnetic field may be increased or decreased by adjusting the electrical current passing through coil 76.

Means 38 for adjustably controlling the amount of current and/or voltage passing through coil 76 is also provided. Due to the electromagnetic construction of magnetic means 28, controlling means 38 also adjustably controls the magnetic field and the resulting magnetic force which is generated around bobbin 68. In other words, controlling means 38 may be adjusted to selectively activate magnetic means 28 which causes stator 66 to become an electromagnet having an adjustable magnetic field 30 thereabout. The effect the magnetic field has on the operation of apparatus 20 will be discussed further below.

Plunger 32 is located longitudinally within handle portion 40 and shaft portion 48 of enclosure 56, and may extend nearly the entire length of apparatus 20. Plunger 32 is limited to longitudinal movement generally along longitudinal axis 52 of housing 26. Stator 66 encircles a portion of the length of plunger 32.

Plunger 32 has a first plunger end 82 that is magnetically connectable to stator 66. For example, in the preferred embodiment, first plunger end 82 is provided with an outwardly radiating flange 83. Flange 83 may be magnetically connected to and detachable from first flange 72 of stator 66. Alternatively, if tube 77 is placed between bobbin 68 and plunger 32, flange 83 may be magnetically connected to and detachable from flange 77'. In other words, flange 83 of plunger 32 is juxtaposed against and magnetically secured to first flange 72 of either bobbin 68 or to flange 77' of tube 77.

In the preferred embodiment, plunger 32 has two separable collinear parts comprising a magnetically reactive hollow plunger 84 and an abutting working plunger 86.

When it is desired to override the safety features designed into the present invention, as when removal of attachment means 22 becomes necessary, working plunger 86 may be urged away from abutting magnetically reactive plunger 84 by reverse plunger 87. As a consequence, working plunger 86 may be moved into operative engagement with ratchet mechanism 36 without being affected by the magnetic field. This feature will be discussed in greater detail further below.

Flexible spring 34 is located within enclosure 56 and extends longitudinally within shaft portion 48 toward ratchet portion 44. A first spring end 88 of flexible spring 34 is operatively secured to plunger 32. Consequently, longitudinal movement of plunger 32 will cause flexible spring 34 to move longitudinally within enclosure 56. Attachment of first spring end 88 to plunger 32 may be accomplished by any appropriate means, such as by using one or more screws, bolts, rivets, pins 90, or similar objects. A remaining distal end 92 of flexible spring 34 defines a forward pawl that is capable of engaging ratchet mechanism 36.

Ratchet mechanism 36 is located within enclosure 56 and is operatively and rotatably secured to housing 26 within ratchet portion 44. Ratchet mechanism 36 has a first and a second shaft or pin 96 and 98, at respective ends thereof, which serve as bearing surfaces that are received by corresponding indentations or seats 100 and 102, respectively, in housing 26. In the preferred embodiment, seat 100 is located in ratchet cover plate or lid 60 which enables easy access to ratchet mechanism 36 and removal thereof when desired.

Rotation of ratchet mechanism 36 within housing 26 defines rotational axis 54. Ratchet mechanism 36 has a plurality of spaced teeth 94 which project radially outward from rotational axis 54 and extend outwardly from ratchet mechanism 36.

Ratchet mechanism 36 further comprises means 104 for engaging attachment means 22. For example, if attachment means 22 is a flat headed screw, engaging means 104 may comprise a flat head screwdriver having a socketed end which is inserted into ratchet mechanism 36. Similarly, engaging means 104 may have any desired shape of screwdriver head, may comprise a conventional socket system wherein a shank thereof is engaged by ratchet mechanism 36, or may take the form of other well-known mechanisms, such as a keyed shaft or cylinder, or the like.

Thus configured, flexible spring 34 is positioned to operatively contact and rotate ratchet mechanism 36. Pivotal rotation of housing 26 in a tightening direction, indicated by arrow 106, causes distal end 92 of flexible spring 34 to engage teeth 94 and urge ratchet mechanism 36 to rotate. Pivotal rotation of housing 26 in an opposite or reverse direction, indicated by arrow 108, causes flexible spring 34 to ride up on teeth 94 and disengage ratchet mechanism 36. Housing 26 is moved in a reverse direction 108 until flexible spring 34 is repositioned with respect to ratchet mechanism 36 for successive rotation in tightening direction 106. Renewed rotation of housing 26 in tightening direction 106 urges flexible spring 34 to reengage teeth 94 and urge ratchet mechanism 36 to rotate.

In other words, during operation, handle portion 40 can be manipulated through a forward stroke or direction 106 to urge flexible spring 34 into contact with external teeth 94 of ratchet mechanism 36. Moving handle portion 40 through a backstroke or reverse direction 108 causes flexible spring 34 to return to a new initial position, ready to be urged against a next successive ratchet tooth 94.

Apparatus 20 can be extremely small. Consequently, a dentist need move handle portion 40 only a very short distance to cause ratchet mechanism 36 to rotate. The required swing and arm of handle portion 40 is also extremely small to accommodate placement and operation within the mouth of a patient.

Figure 14:
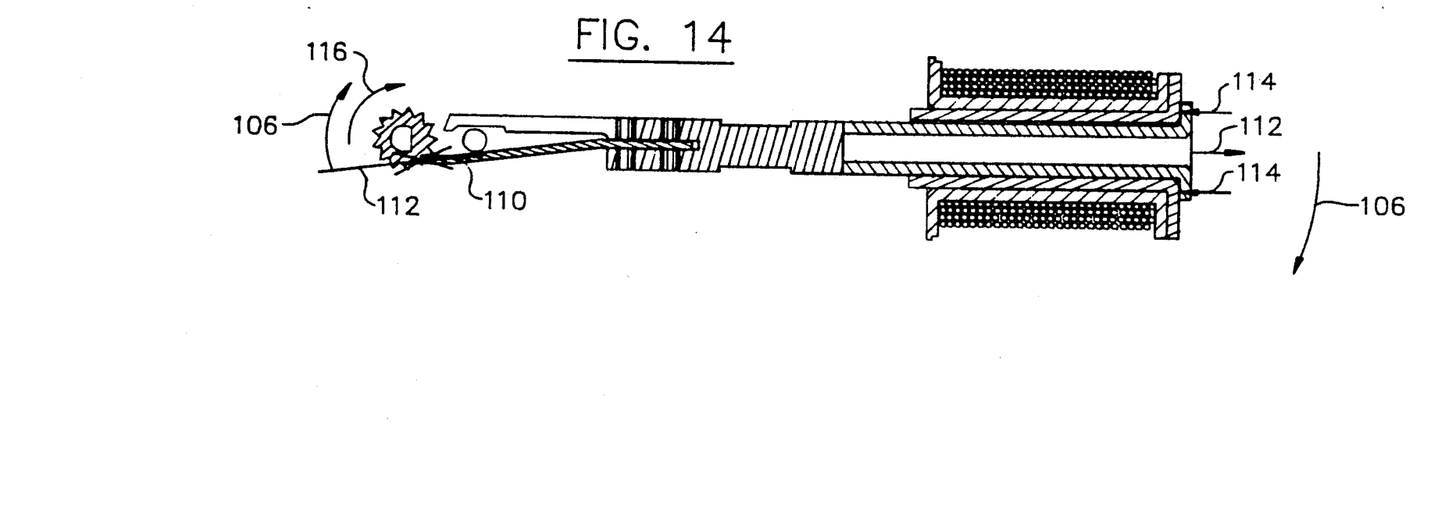
FIG. 14 is a schematic view of the various forces exerted upon and by the rachet mechanism, flexible spring, plunger, and stator.

Referring now to the FIG. 14, as handle portion 40 is rotated in tightening direction 106, distal end 92 of flexible spring 34 exerts an operative force 110 against teeth 94. In response to the exertion of operative force 110, teeth 94 exert a reactive force 112 against distal end 92 of flexible spring 34.

Reactive force 112 is transmitted through the length of flexible spring 34 to plunger 32. Reactive force 112 is then transmitted through the length of plunger 32 to a magnetic connection between stator 66 and first plunger end 82. For example, reactive forces 112 exerted against distal end 92 of flexible spring 34 are directly transferred to flange 83 of plunger 32; whereupon, stator 66 exerts an attractive retaining magnetic force 114 on flange 83.

Flexible spring 34 is capable of rotating ratchet mechanism 36 in tightening direction 106 as long as reactive force 112 is less than or equal to magnetic force 114. However, flexible spring 34 will disengage and become inoperative and incapable of rotating ratchet mechanism 36 in tightening direction 106 when reactive force 112 is greater than magnetic force 114, which causes flange 83 to decouple from stator 66 and thereby retract distal end 92 away from teeth 94.

Means 38 for adjustably controlling the amount of current and/or voltage passing through coil 76 also controls the magnetic field and magnetic force 114 near flange 83 of plunger 32. Consequently, the amount of torque force 116 that apparatus 20 is capable of exerting upon attachment means 22 is directly related to the controlled current and/or voltage passing through coil 76. In general, if torque force 116 exceeds magnetic force 114 between flange 83 and flange 77', plunger 32 will decouple from stator 66 and apparatus 20 will be rendered inoperative.

The amount of current flowing through stator 66 will determine the amount of torque force 116 needed to decouple plunger flange 83 from stator flange 77'. As a result, an extremely precise amount of current and voltage may be used and continuously monitored and regulated to obtain a precise maximum torque force 116 for apparatus 20. Maximum torque force 116 may be easily adjusted without actually observing ratchet mechanism 36 in operation. Adjustments may be made instantaneously without having to remove apparatus 20 from attachment means 22.

When a desired torque force 116 is achieved, as defined by a predetermined magnetic field, plunger flange 83 will simply decouple from stator flange 77'. When freed, plunger 32 and flexible spring 34 move away from ratchet mechanism 36 and become inoperative. Flexible spring 34 can continue to rotate ratchet mechanism 36 only until torque force 116 on ratchet mechanism 36 is sufficient to decouple plunger flange 83 from stator flange 77' and thereby render apparatus 20 inoperative. Unless the manual override feature is instigated, it is impossible to over-torque a prosthetic device past a predetermined setting as described above.

If a greater torque force 116 is required, the practitioner can increase the magnetic field in accurate, gradual, and/or stepped increments. After increasing the current and/or voltage to stator 66, housing 26 is rotated to allow plunger flange 83 to recontact stator flange 77' and thereby reset apparatus 20 for continued operation.

Figure 11:
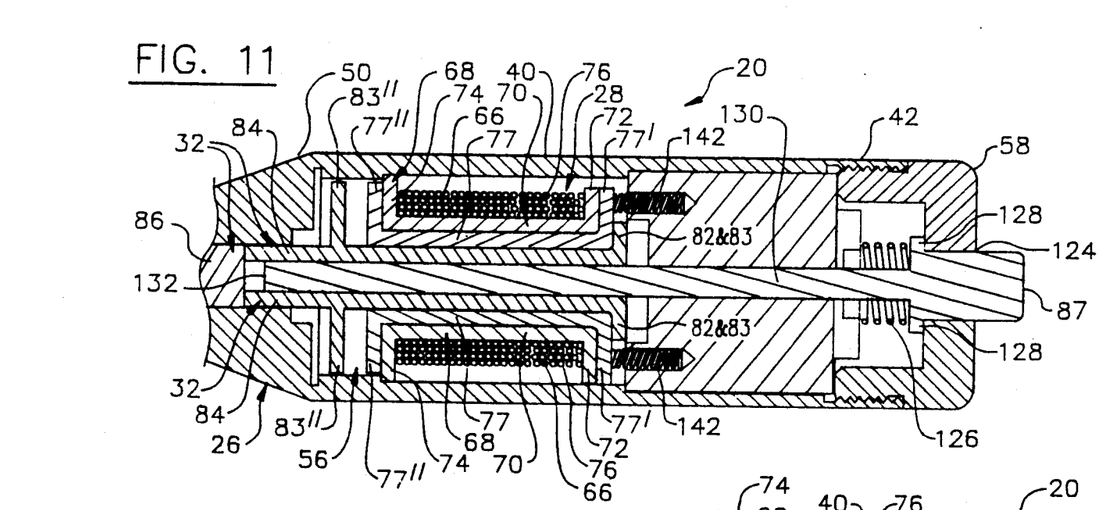
FIG. 11 is a partial, cross-sectional, side-elevational view of a second embodiment of the invention, wherein the stator is provided with two opposed flanges and the plunger is provided with two similarly opposed but further spaced apart flanges that define the limits of longitudinal movement of the plunger flange.
Figure 12:
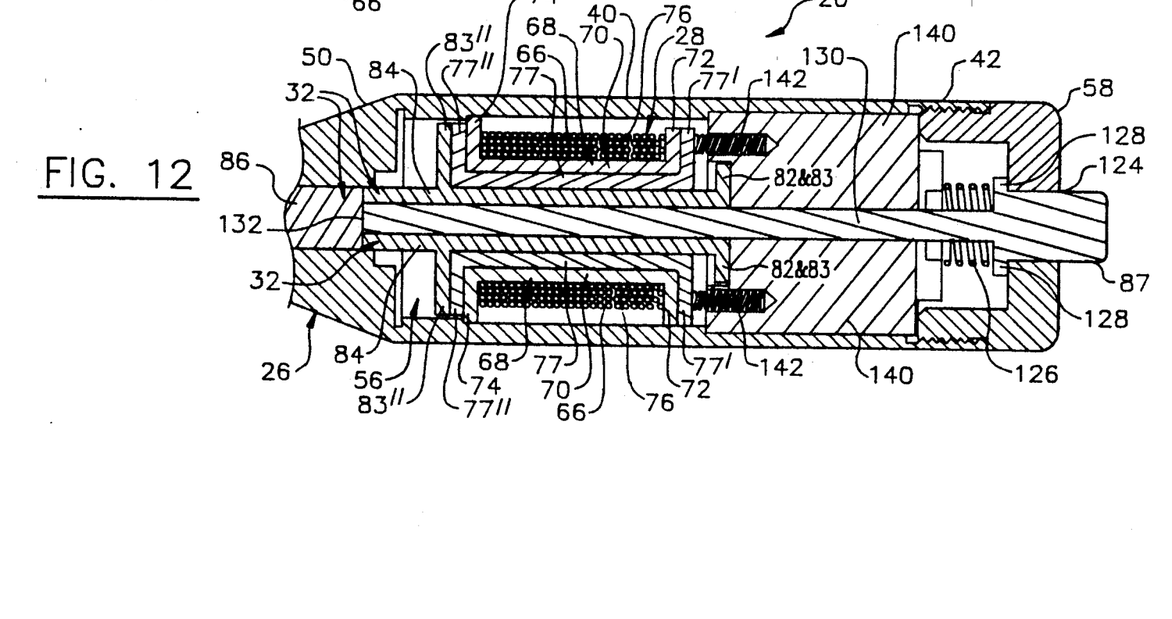
FIG. 12 is a partial, cross-sectional, side-elevational view of the second embodiment of the invention as seen in FIG. 11, with the plunger flange urged away from the ratchet mechanism.
Figure 13:
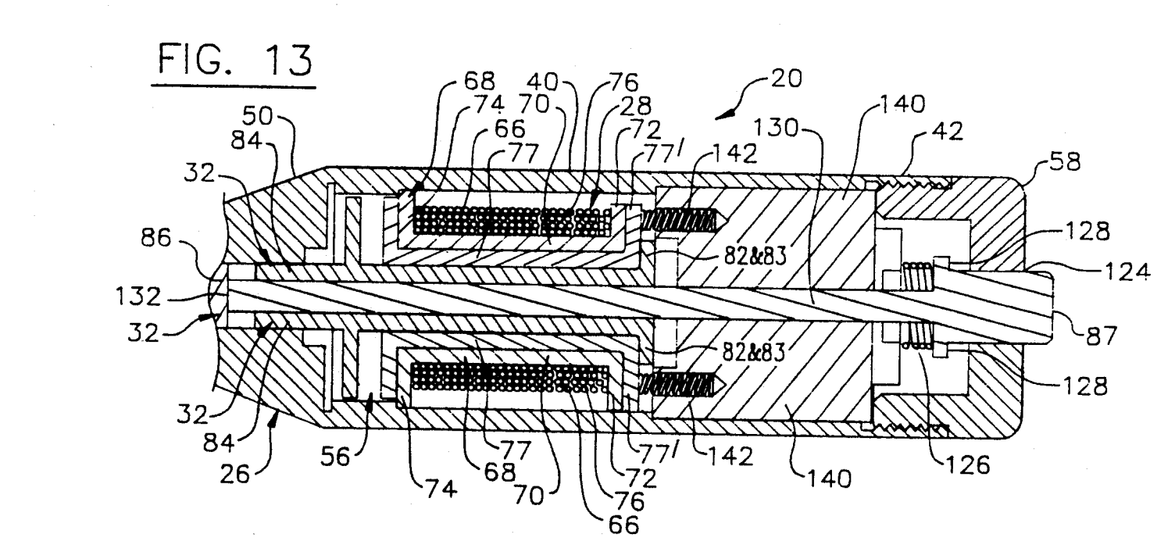
FIG. 13 is a partial, cross-sectional, side-elevational view of the second embodiment of the invention as seen in FIGS. 11 and 12, illustrating the activation of the reverse plunger to override the function of the electromagnetic field.

In an alternative embodiment as illustrated in FIGS. 11, 12, and 13, plunger 32 and stator 66 are further provided with means to magnetically urge longitudinal movement of plunger 32 alternately back and forth within enclosure 56. Movement of plunger 32 mechanically automates alternating engagement and retraction of flexible spring 34 against successive teeth 94 of ratchet mechanism 36, thereby causing ratchet mechanism 36 to rotate until reactive force 112 is greater than magnetic force 114 which causes plunger 32 to become disengaged from stator 66.

To accomplish the objective of this alternative embodiment, stator 66 is provided with two opposed stator flanges 77' and 77" that are positioned at opposite ends of hollow tube 77. Plunger 32 is similarly provided with two flanges 83 and 83". A first plunger flange 83 is placed in close proximity to a first stator flange 77'. A second plunger flange 83" is placed in close proximity to a second stator flange 77". The distance between first plunger flange 83 and second plunger flange 83" will be larger than the distance between first stator flange 77' and second stator flange 77".

The current flowing through stator 66 can be reversed as desired to create an alternating electric solenoid motor. During operation, stator flanges 77' and 77" will either have an attractive or repulsive force associated therewith. Consequently, stator flanges 77' and 77" will reciprocally pull the respective corresponding plunger flange 83 or 83" close thereto or push the plunger flange away therefrom.

Since flexible spring 34 is partially flexible, longitudinal movement of plunger 32 back and forth within housing 26 will cause flexible spring 34 to successively urge ratchet mechanism 36 into motion. The resulting action is the automated mechanical rotation of ratchet mechanism 36 until a desired maximum torque force 116 is achieved, upon which plunger 32 becomes disengaged from stator 66 as described above.

In a different application, apparatus 20 may be used to test an unknown torque used on a particular attachment means 22. For example, since the current flowing through stator 66 to create the magnetic field can easily be measured, a current which just barely decouples plunger flange 83 from stator flange 77' can be used to determine the precise torque force 116 used on attachment means 22.

The present invention is also provided with an override feature that allows for operation of the device as a traditional ratchet system without being dependent upon electro-mechanical operation. This feature can be used in situations where the electrical power source has become deactivated, such as in times of a power failure, or when manual override of apparatus 20 is desired.

When the electro-mechanical features of apparatus 20 are overridden, plunger 32 may be extended toward ratchet mechanism 36 to facilitate the removal of attachment means 22. To accomplish this task, reverse plunger 87 has a first end 122 which extends outwardly through an orifice 124 in housing 26. More particularly, orifice 124 is preferably placed in end cap 58. Reverse plunger 87 is held in place against housing 26 or end cap 58 by a compression spring 126. To prevent the passage and escape of reverse plunger 87 through orifice 124, reverse plunger 87 is provided with a flange 128 having a wider diameter than the diameter of orifice 124.

Reverse plunger 87 also has an elongated shank 130 that passes through the hollow center of magnetically reactive plunger 84 to be near to or butt up against abutting working plunger 86.

During regular operation of apparatus 20, reverse plunger 87 remains in an initial inoperative position shown in FIGS. 7, 9, 11, and 12.

When the override feature is desired, first end 122 of reverse plunger 87 is pushed or urged into enclosure 56 of housing 26. This action causes a second end 132 of reverse plunger 87 to contact and urge working plunger 86 toward ratchet mechanism 36. Once working plunger 86 is urged a designated distance, flexible spring 34 is automatically urged past and away from teeth 94 of ratchet mechanism 36.

Figure 8:
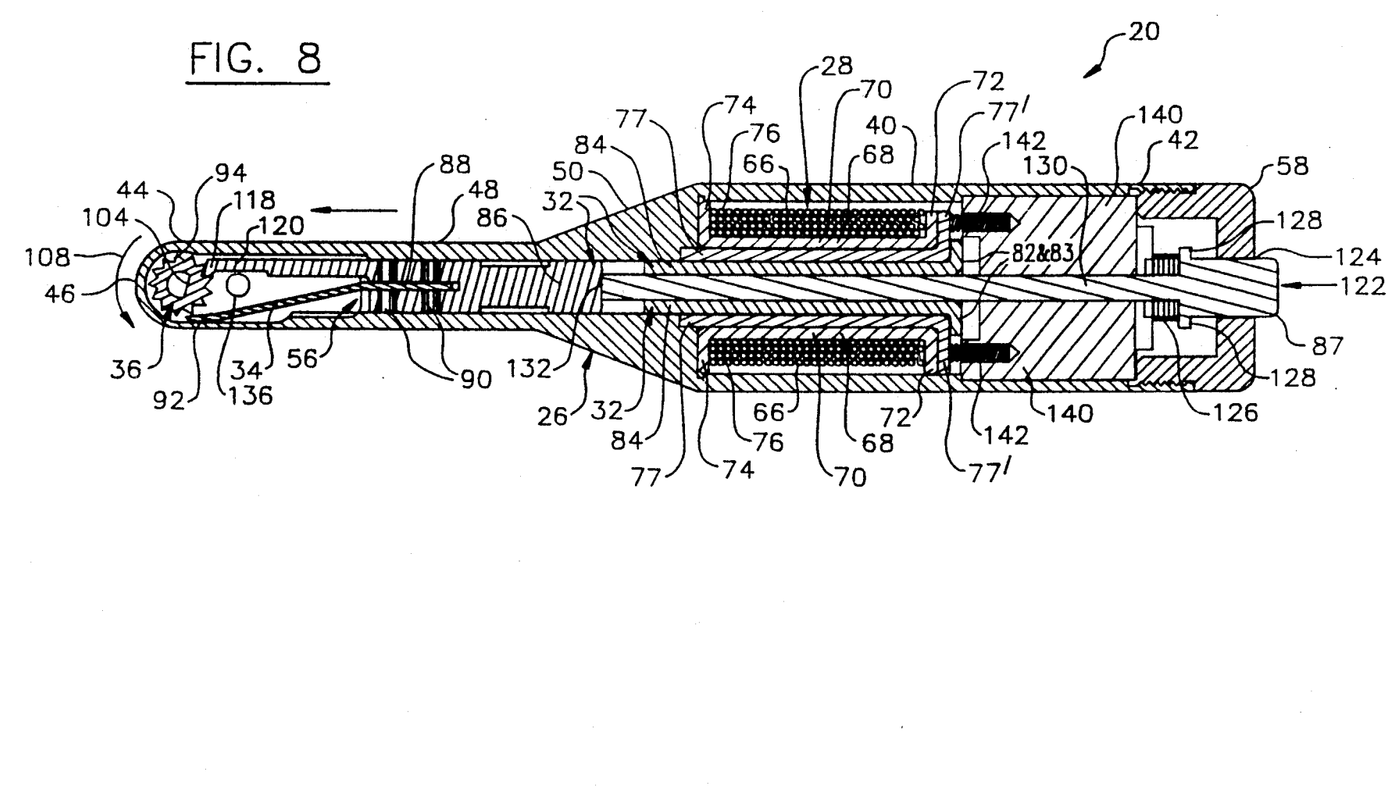
FIG. 8 is a cross-sectional view of the invention as seen along a plane defined by line 7—7 in FIG. 1, wherein the reverse plunger is activated to override the operation of the flexible spring and urge the ratchet mechanism to rotate in an opposite direction.

A prong or reverse pawl 118 extends from a second distal or terminal end 120 of plunger 32. When urged forward, such that flexible spring 34 is disengaged, reverse pawl 118 engages teeth 94 to rigidly lock or secure ratchet mechanism 36 against movement with respect to housing 26.

Manual rotational movement of handle portion 40 urges ratchet mechanism 36 to similarly rotate without dependency upon the magnetic field. If handle portion 40 is rotated in an opposite loosening direction 108, apparatus 20 can be used to remove attachment means 22 from material 24.

Other elements illustrated in the drawings include an attaching bolt 134 or screw which passes through a hole 136 in housing 26 to engage a threaded bore hole 138 and thereby removably secure cover plate 60 to housing 26.

To securely hold stator 66 within enclosure 56, apparatus 20 may be provided with a spacer 140 that is positioned between stator 66 and end cap 58. Compression spacer springs 142, bolts, pins, or the like may also be used to absorb any slack or lack of tolerances that may occur during the manufacturing process. Compression spacer springs 142 may be positioned between stator 66 and spacer 140.

Figure 6:
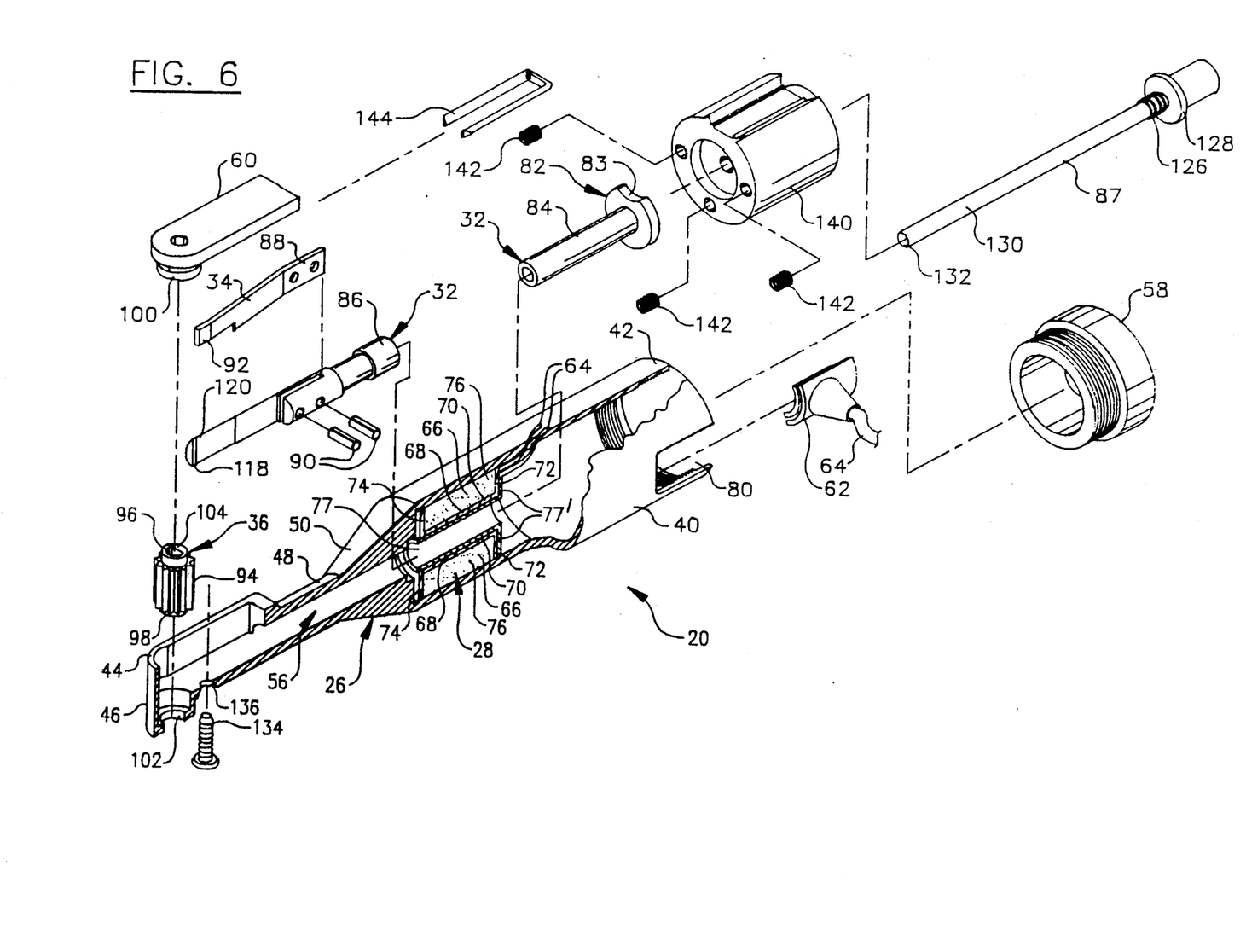
FIG. 6 is a partially-sectioned, exploded, isometric view of the first embodiment of the invention, wherein a portion of the housing is removed to better illustrate the interior enclosure or cavity of the housing.
Figure 7:
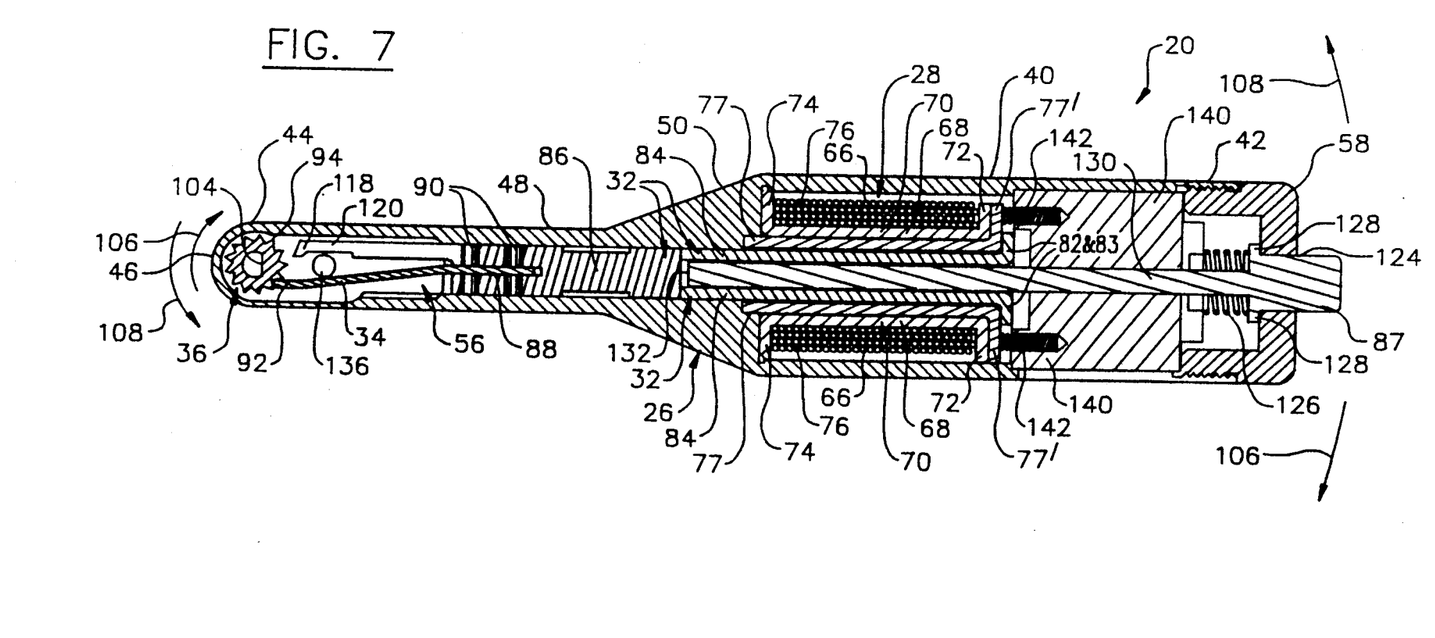
FIG. 7 is a cross-sectional view of the invention as seen along a plane defined by line 7—7 in FIG. 1, wherein the plunger flange is urged against the stator flange thereby forcing the plunger and flexible spring toward the ratchet mechanism to urge the ratchet mechanism to rotate.

Means 144 for clipping or securing ratchet mechanism 36 to cover plate or lid 60 may also be provided. For example, as shown in FIGS. 6 and 9, clipping means 144 may comprise a U-shaped clip which engages a channel in cover plate 60 and a slot or groove (not shown) in pin 96 of ratchet mechanism 36. Thus configured, when cover plate 60 is removed from housing 26, clipping means 144 retains ratchet mechanism 36 thereto causing ratchet mechanism 36 to be withdrawn from enclosure 56.

The means and construction disclosed herein are by way of example and comprise primarily the preferred form of putting the invention into effect. Although the drawings depict preferred and alternative embodiments of the invention, other embodiments have been described within the preceding text. One skilled in the art will appreciate that the disclosed device may have a wide variety of shapes and configurations. Additionally, persons skilled in the art to which the invention pertains might consider the foregoing teachings in making various modifications, other embodiments, and alternative forms of the invention.

It is, therefore, to be understood that the invention is not limited to the particular embodiments or specific features shown herein. To the contrary, the inventor claims the invention in all of its forms, including all alternatives, modifications, equivalents, and alternative embodiments that fall within the legitimate and valid scope of the appended claims, appropriately interpreted under the Doctrine of Equivalents.

INDUSTRIAL APPLICABILITY

The present invention may be used within a wide variety of professions and industries, wherein simple, reliable, easily used apparatus and processes are needed to rotate and thereby insert or remove a bolt, nut, screw, prosthesis, or other means of attachment to or from a desired medium or material. The apparatus of this invention is compact, functional, unobtrusive, efficient, reusable, durable, rugged, easily constructed, and inexpensive and economical to manufacture. Traditional or nontraditional means for attachment may be used. The present invention not only increases the speed and simplifies the procedure to rotate, and thereby insert or remove such means of attachment, it also provides a torque wrench which can be automated and requires less access room for operation.

Although the invention has a wide range of applications, the invention has a special application in surgical procedures, wherein a screw, bolt, nut, or prosthesis must be secured to bone. The present invention permits such procedures to be accomplished in areas of extremely limited access. The device and process may even be used within a very small, deep access opening or incision, with minimum damage to adjacent bone structure and soft tissue.

What is claimed is:

1. An apparatus for turning attachment means, within a material, said apparatus comprising:
   (a) an elongated housing defining an enclosure, said housing having a handle portion at one end, a ratchet portion at an opposite end and an elongated shaft portion, said elongated shaft portion being positioned between said handle portion and said ratchet portion;
   (b) means for producing a magnetic field, said magnetic field means having a stator located within said enclosure, said stator being secured to said housing;
   (c) an elongated plunger located within said enclosure, said plunger extending generally longitudinally within at least a portion of said handle portion and within at least a portion of said shaft portion, said plunger having a first plunger end that is magnetically connectable to said stator;
   (d) an elongated spring located within said enclosure, said spring extending generally longitudinally within at least a portion of said shaft portion toward said ratchet portion, said spring having a first spring end operatively secured to said plunger; and
   (e) a ratchet mechanism located within said enclosure, said ratchet mechanism being operatively and rotatably secured to said housing within said ratchet portion, said ratchet mechanism having an axis of rotation, said ratchet mechanism having a plurality of spaced teeth projecting radially outward from said ratchet mechanism, said spring further having a distal end, said distal end of said spring being capable of engaging said teeth and urging said ratchet mechanism to rotate when said plunger is magnetically secured to said stator and an operative force is applied to said housing to pivotally rotate said housing about said axis in a tightening direction, said operative force being transmitted to said plunger through magnetic engagement of said plunger with said stator, said operative force being transmitted to said spring through mechanical engagement of said spring with said plunger, said operative force being transmitted to said ratchet mechanism through mechanical engagement of said spring with said ratchet mechanism, said operative force being further transmitted to the attachment means through mechanical engagement of the attachment means with said ratchet mechanism, said distal end of said spring becoming disengaged from said teeth when said housing is pivotally rotated about said axis in an opposite or reverse direction, rotation of the attachment means within the material imparting a reactive force that is transmitted to said plunger through said ratchet mechanism and said spring, said plunger becoming disengaged from said stator when either said reactive force or said operative force generally exceed a magnetic force defined by magnetic engagement of said plunger with said stator.

2. The apparatus of claim 1, wherein said stator is located within said handle portion.

3. The apparatus of claim 1, wherein at least a portion of said plunger is movable toward said ratchet mechanism irrespective of whether or not said plunger is magnetically secured to said stator, said plunger being capable of urging said spring to disengage from said teeth when said plunger is moved toward said ratchet mechanism, said plunger further comprising a terminal end defining a reverse pawl, said reverse pawl being capable of engaging said teeth when said plunger is further moved toward said ratchet mechanism, said reverse pawl being capable of urging said ratchet mechanism to rotate when said housing is pivotally rotated about said axis.

4. The apparatus of claim 1, wherein said plunger and said stator are further provided with means to magnetically urge longitudinal movement of said plunger back and forth within said enclosure, movement of said plunger allowing engagement and retraction of said spring against successive teeth of said ratchet mechanism mechanically automating rotation of said ratchet mechanism until said reactive force or said operative force generally exceeds said magnetic force causing said plunger to become disengaged from said stator.

5. The apparatus of claim 1, wherein said plunger further comprises a plunger flange positioned near said stator, said stator further having a stator flange, said stator flange selectively magnetically engaging said plunger flange, said stator encircling a portion of a length of said plunger.

* * * * *